(12) United States Patent
Ruiter

(10) Patent No.: US 8,328,563 B2
(45) Date of Patent: Dec. 11, 2012

(54) ELECTROCARDIOGRAPH AND BLOOD PRESSURE SIGNALS SIMULATOR

(75) Inventor: Karl Ruiter, Honolulu, HI (US)

(73) Assignee: Pronk Technologies, Inc., Pasadena, CA (US)

( * ) Notice: Subject to any disclaimer, the term of this patent is extended or adjusted under 35 U.S.C. 154(b) by 105 days.

(21) Appl. No.: 13/021,509

(22) Filed: Feb. 4, 2011

(65) Prior Publication Data

US 2011/0124248 A1 May 26, 2011

Related U.S. Application Data

(62) Division of application No. 11/841,245, filed on Aug. 20, 2007, now Pat. No. 7,917,774.

(60) Provisional application No. 60/823,125, filed on Aug. 22, 2006.

(51) Int. Cl.
*H01R 33/00* (2006.01)

(52) U.S. Cl. .......................................................... 439/37

(58) Field of Classification Search ................... 439/37, 439/909, 884
See application file for complete search history.

(56) References Cited

U.S. PATENT DOCUMENTS

| | | | | |
|---|---|---|---|---|
| 4,204,261 A | | 5/1980 | Ruszala et al. | |
| 4,253,721 A | * | 3/1981 | Kaufman | 439/372 |
| 4,267,576 A | * | 5/1981 | Power et al. | 703/13 |
| 5,326,272 A | * | 7/1994 | Harhen et al. | 439/86 |
| 5,348,488 A | | 9/1994 | Green et al. | |
| 5,562,607 A | * | 10/1996 | Gyory | 604/20 |
| 5,924,979 A | | 7/1999 | Swedlow et al. | |
| 6,038,578 A | | 3/2000 | Fogg | |
| 6,077,227 A | * | 6/2000 | Miesel et al. | 600/486 |
| 7,364,440 B2 | * | 4/2008 | Gobron et al. | 439/77 |
| 7,445,522 B2 | * | 11/2008 | Burnes et al. | 439/725 |
| 7,559,899 B2 | * | 7/2009 | Lo et al. | 600/502 |
| 7,917,774 B2 | * | 3/2011 | Ruiter | 713/300 |
| 7,950,971 B2 | * | 5/2011 | Hobet et al. | 439/822 |
| 8,197,276 B2 | * | 6/2012 | Egloff et al. | 439/268 |
| 2003/0105403 A1 | | 6/2003 | Istvan et al. | |
| 2004/0113790 A1 | | 6/2004 | Hamel et al. | |
| 2004/0147847 A1 | | 7/2004 | Ng et al. | |

FOREIGN PATENT DOCUMENTS

WO    WO-01/85019 A2    11/2001

OTHER PUBLICATIONS

Examination Report for Application No. GB0904265.6 dated Nov. 24, 2010.
Examination Report for Application No. GB0904265.6 dated May 3, 2011.
Search Report for Application No. GB1103638.1 dated Apr. 28, 2011.
International Search Report for Serial No. PCT/US2007/076413 mailed Apr. 17, 2008.
Notice of Allowance for U.S. Appl. No. 11/841,245 mailed Nov. 30, 2010.

\* cited by examiner

*Primary Examiner* — Phuong Dinh

(74) *Attorney, Agent, or Firm* — Michael Blaine Brooks, PC; Pejman Yedidsion; Christopher Weiss

(57) ABSTRACT

System, methods, and apparatuses produce simulated human physiological waveforms such as electrocardiograph (ECG) and blood pressure signals where the microcontroller and/or digital-to-analog converters may be switched to a lower power-consuming state by programmable instructions and switched on in response to a programmable sleep timer.

2 Claims, 6 Drawing Sheets

ELECTROCARDIOGRAPH AND BLOOD PRESSURE SIGNALS SIMULATOR

CROSS-REFERENCE TO RELATED APPLICATIONS

This application is a divisional of U.S. patent application Ser. No. 11/841,245 filed Aug. 20, 2007 now U.S. Pat. No. 7,917,774 which claims the benefit of U.S. Provisional Patent Application Ser. No. 60/823,125 filed Aug. 22, 2006, entitled "ELECTROCARDIOGRAPH AND BLOOD PRESSURE SIGNALS SIMULATOR," which is hereby incorporated by reference herein for all purposes.

BACKGROUND

The field of endeavor to which the invention, in its several embodiments, generally pertains is simulating physiological signals and particularly pertains to devices, systems and methods for producing simulated human electrocardiograph (ECG) and blood pressure signals.

A series of waveforms may be selected and generated to test and calibrate devices which respond to waveform signals. A typical waveform signal simulating device has one or more, typically digitized, waveforms in non-volatile memory such as a read-only memory (ROM). The operator of the simulating device may request, via an operator interface, a digitized waveform that is then recalled from the memory and processed through a digital-to-analog converter (DAC). The converted signal, as an analog waveform signal, may then be transmitted to the device that responds to the waveform, such as an ECG monitor under test, for example, for purposes of evaluation and calibration.

SUMMARY

The invention, in its several embodiments, includes exemplary physiological waveform simulator embodiments that may comprise a sleep timer having a sleep timer oscillator; and a microcontroller having its own microcontroller oscillator, and the exemplary simulator further comprises: (a) a means for waking that may include the microcontroller, particularly its oscillator, receiving a wake-up signal from the sleep timer; (b) a means for writing a portion of a physiological waveform profile that may include the microcontroller sending signals representative of portions of the profile of the physiological waveform to a circuit that convert the discrete signals into analog form; and (c) a means for sleeping that may include the microcontroller itself executing an instruction to turn its oscillator to a low power-consuming state or off state or otherwise a sleep state. When the microcontroller is turned to a low power-consuming state, that is, consuming a lower power than the awake state, a sleep timer may be invoked and the invocation of the sleep timer may be done when a time slope of the physiological waveform profile becomes zero. The means for writing may comprise a writing module for writing a plurality of physiological waveform values representative of a physiological waveform profile to a digital-to-analog converter and/or may comprise a writing module for executing one or more writing events including a first writing event wherein the microcontroller transmits a first physiological waveform value based on the physiological waveform profile; and wherein the microcontroller is placed in a low power-consuming state after the writing module transmits the first physiological waveform value.

In the simulator embodiments, the writing module for executing one or more writing events may further include a second writing event where the microcontroller wakens, now with its oscillator causing it to consumer power higher than the previous sleep state, and transmits a second physiological waveform value based on the physiological waveform profile, then the microcontroller, particularly its oscillator, may be placed in a lower power-consuming state, i.e., lower power consumption than the wake state and may also be termed a sleep state, after the writing module transmits the second physiological waveform value. The time interval between the first writing event and the second writing event may be based on the physiological waveform profile. For example, the time interval between the first writing event and the second writing event may be inversely related to non-zero time rates of change in the physiological waveform profile or the magnitude of the physiological waveform profile.

In the simulator embodiments, the writing module for executing one or more writing events may include a first writing event where the microcontroller transmits a first physiological waveform value based on the physiological waveform profile, to a digital-to-analog converter, and where the microcontroller, particularly its oscillator, may be placed in a low power-consuming state after the writing module transmits the first physiological waveform value, and where the digital-to-analog converter is adapted to be placed in an on state to receive the first transmitted physiological waveform value and the digital-to-analog converter is adapted to be placed in a low power-consuming state after receiving the first physiological waveform value transmission. In addition, the simulator embodiments may further include a sample-and-hold circuit for receiving an output of the digital-to-analog converter prior to the digital-to-analog converter being placed in a low power-consuming state. The writing module for executing one or more writing events further may include means for executing a second writing event where the microcontroller transmits a second physiological waveform value to a digital-to-analog converter and where the digital-to-analog converter is adapted to be placed in an on state to receive the second transmitted physiological waveform value and the digital-to-analog converter may be adapted to be placed in an low power-consuming state after receiving the second physiological waveform value transmission. The time interval between the first writing event and the second writing events may be inversely related to non-zero time rates of change in the physiological waveform profile. Further, the digital-to-analog converter may be output-enabled so as to output a value for the duration of time based on the physiological waveform profile. The digital-to-analog converter output-enabled duration may be based on a magnitude or a time rate of change of the physiological waveform profile.

The physiological waveform simulator may be embodied to include an electrocardiograph (ECG) ladder. For example, the simulator may comprise a microcontroller; the ECG ladder having a high side and a low side, a first DAC; and a second DAC; wherein the first DAC drives the high side of the ECG ladder via a first hold circuit, and the wherein the second DAC drives the low side of the ECG ladder via a second hold circuit. In these embodiments, biases that draw additional power are not required.

The physiological waveform simulator may also be embodied as a microcontroller comprising a means for writing a physiological waveform value to a DAC where the DAC has a reference voltage and where a positive supply voltage to the physiological waveform simulator is drawn from a monitor excitation signal and a negative supply voltage to the physiological waveform simulator and is drawn from an output of a charge pump inverter driven by the monitor excitation signal. In addition, the monitor excitation signal may be rectified in some embodiments.

Exemplary methods of energy management for a physiological waveform simulator may include the steps of: (a) waking the simulator's microcontroller, particularly its oscillator, from a sleep mode via a sleep timer; (b) transmitting a first physiological waveform value, based on physiological waveform profile, to at least one of a first receiving digital-to-analog converter and a second receiving digital-to-analog converter; (c) putting the microcontroller into the sleep mode after the transmission of the first physiological waveform value; and (d) enabling at least one of: (i) the first receiving digital-to-analog converter to be powered for a duration to drive a first hold circuit and (ii) the second receiving digital-to-analog converter to be powered for a duration to drive a second hold circuit. The enabling duration of the at least one of the first receiving digital-to-analog converter and the second receiving digital-to-analog converter may be based on the magnitude or time rate of change of the physiological waveform profile. When a monitor excitation source is available, the exemplary method may further include the step of powering a portion of the physiological simulator circuitry via the monitor excitation source. In addition, the exemplary method may further include the steps of: (a) waking, after a time interval that may be based on the physiological waveform profile, the microcontroller, particularly its oscillator, from a sleep mode via the sleep timer; and (b) transmitting a second physiological waveform value, based on a physiological waveform profile, to at least one of: a first receiving digital-to-analog converter and a second receiving digital-to-analog converter. The exemplary method may include inverting the monitor excitation source to drive at least one digital-to-analog converter.

Additional exemplary methods of energy management for a physiological waveform simulator may include the steps of: (a) waking the simulators microcontroller, particularly its oscillator, from a sleep mode via a sleep timer; (b) writing a first physiological waveform value, based on physiological waveform profile; and (c) putting the microcontroller, particularly its oscillator, into the sleep mode after the writing of the first physiological waveform value. The exemplary method may further include the steps of: (a) waking, after a time interval based on the physiological waveform profile, the simulator's microcontroller, particularly its oscillator, from a sleep mode via the sleep timer; and (b) writing a second physiological waveform value, based on a physiological waveform profile. When a monitor excitation source is available, the method may include the step of powering a portion of the simulator via the monitor excitation source and may include the step of inverting the monitor excitation source to drive at least one digital-to-analog converter.

The several simulator and method embodiments may be controlled by a user via an interface of a display system. For example, a display system for a physiological waveform simulator having at least two output modes may include: (a) a button; (b) a lighting circuit; (c) an output mode lamp array comprising two or more lamps. Operationally, the depression and release of the button may advance the physiological waveform simulator to a successive output mode and may switch the lighting circuit to a lamp associated with the successive output mode and, for at least one of the output modes, a depression and continued depression of the button may advance the physiological waveform simulator to a successive waveform output series of the at least one output mode. Another interface or display system embodiment for a physiological waveform simulator having at least two output modes, the physiological waveform simulator may include different operational features, such as where a double click of the button advances the physiological waveform simulator to a successive output mode and switches the lighting circuit to a lamp associated with the successive output mode, and, for at least one of the output modes, a single click of the button advances the physiological waveform simulator to a successive waveform output series of the at least one output mode.

Several simulator embodiments may be connected to a patient monitor, for example, via an electrical connector. Accordingly, the physiological waveform simulator may further include or make use of an electrical connector receiving system for the physiological waveform simulator that includes: (a) a snap portion comprising: (i) a disc portion having a top side, a bottom side and an edge; and (ii) an inverted frustroconical portion fixedly attached to the top side of the disc portion; and (b) a mounting element having a planar surface proximate to a first aperture, which may be, for example, an arcuate aperture or trough; and wherein the bottom side of the disc portion is proximate to the planar surface of the mounting element, and a first sector of the bottom side of the disc portion extends over a portion of the first aperture. In some embodiments of the electrical connector receiving system, the planar surface of the mounting element is interposed between the first aperture and a second aperture, which may be, for example, an arcuate aperture or trough; and wherein a second sector of the bottom side of the disc portion extends over a portion of the second aperture.

BRIEF DESCRIPTION OF THE DRAWINGS

Reference is now made to the following description taken in conjunction with the accompanying drawings, in which.

DETAILED DESCRIPTION

Figure 1:
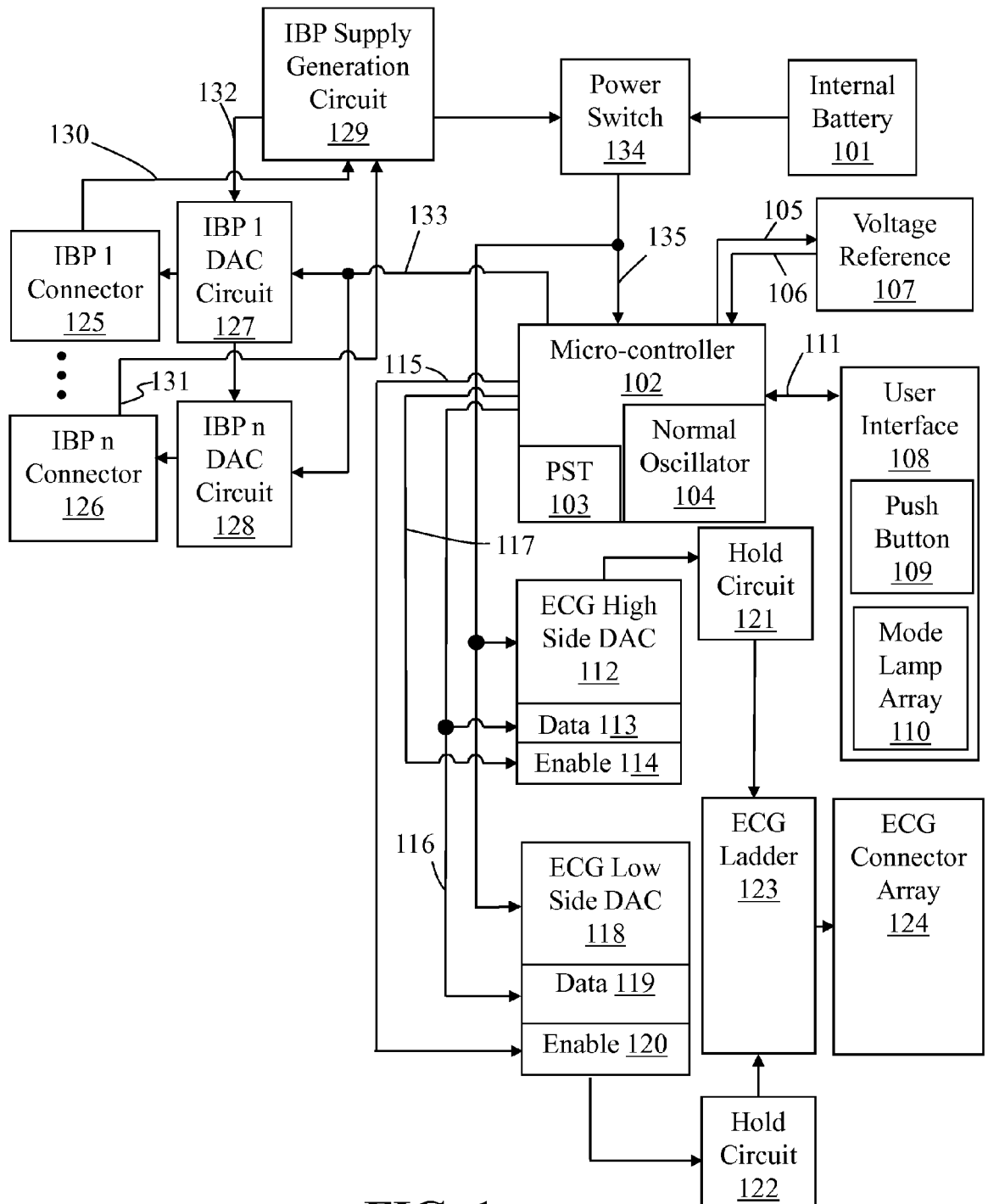
FIG. 1 is an exemplary functional block diagram of an embodiment of the present invention.

A block diagram of an exemplary embodiment of the present invention is shown in FIG. 1. A power supply, external battery, or as shown in FIG. 1, an internal battery 101, provides power to a processing unit such as a microcontroller 102 through, what is shown in this example as a power switch 134. The microcontroller executes instructions at one or more rates based on its oscillator 104, which preferably is an oscillator that can be switched into a low power-consuming state by programmable instructions. In the event the oscillator may be switched to low power-consuming, the microcontroller ceases execution of instructions until a programmable sleep timer (PST) 103, counts down or times out using a rate of a second oscillator, for example, an oscillator that is run separately from the normal oscillator 104 of the microcontroller 102.

ECG simulation may be accomplished via one or more circuits that output analog signals based in discrete inputs, which may be accomplished, for example, by dual digital-to-analog converters (DACs) 112 and 118, where of these two DACs, the ECG High Side DAC 112 drives the high side of the ECG ladder 123 via a first hold circuit 121, and the ECG Low Side DAC 118 drives the low side of the ECG ladder via a second hold circuit 122. This dual DAC scheme allows for bipolar ECG output signals while using a single positive supply, and with both output signals nominally at ground. Each DAC has a data input connection, i.e., an ECG High Side DAC data input 113 and an ECG Low Side DAC data input 119. Both of these date inputs 113, 119 connect 116 the DACs to the micro-controller 102. In addition, an ECG High Side DAC input signaling 117 and an ECG Low Side DAC input signaling 115 may place each respective DAC into a very low or zero power consumption mode 114 and 120 under the enabling control of the microcontroller via the input signaling 115, 117. The ECG ladder 123 is connected to the ECG connector array 124 where the signals are made available to the user. The ECG ladder 123 creates various linearly scaled versions of the ECG signal, each of which is connected to one or more positions of the ECG connector array 124, in order to mimic or otherwise simulate the signals seen generated by human patients at the various commonly used electrode placement locations.

When invasive blood pressure (IBP) simulation is desired, the user connects transducer cables to the IBP connectors, i.e., IBP1 connector 125 through IBPn connector 126. These transducer cables will provide one of several different transducer excitation signals, which are routed to the IBP supply generation circuit 129 via IBP1 signal path 130 through IBPn signal path 131. The IBP supply generation circuit 129 supplies positive and negative supply voltages 132 to the IBP1 DAC circuit 127 through the IBPn DAC circuit 128, and a positive supply voltage to the power switch 134, such that while IBP simulation is occurring, no current need be drawn from the internal battery 101. The IBP1 DAC circuit 127 and the IBPn DAC circuit 128 are shown in this example as being driven by the microcontroller 102 via a signal path 133.

A voltage reference 107 is normally off, but may be turned on by the micro-controller intermittently via a signal path 105 and its output read via signal path 106 and passed via an analog-to-digital (ADC) that may be internal to the microcontroller. This reading of voltage allows the microcontroller to assess the supply voltage 135 and adjust the data values written to the ECG DACs 112, 118 such that the ECG output waveform is of constant size irrespective of moderate variations in supply voltage. A simplified user interface 108 may be connected 111 to the microcontroller 102 and may include a single push button 109 and a single mode indicator lamp or an array of mode indicator lamps 110.

Figure 2:
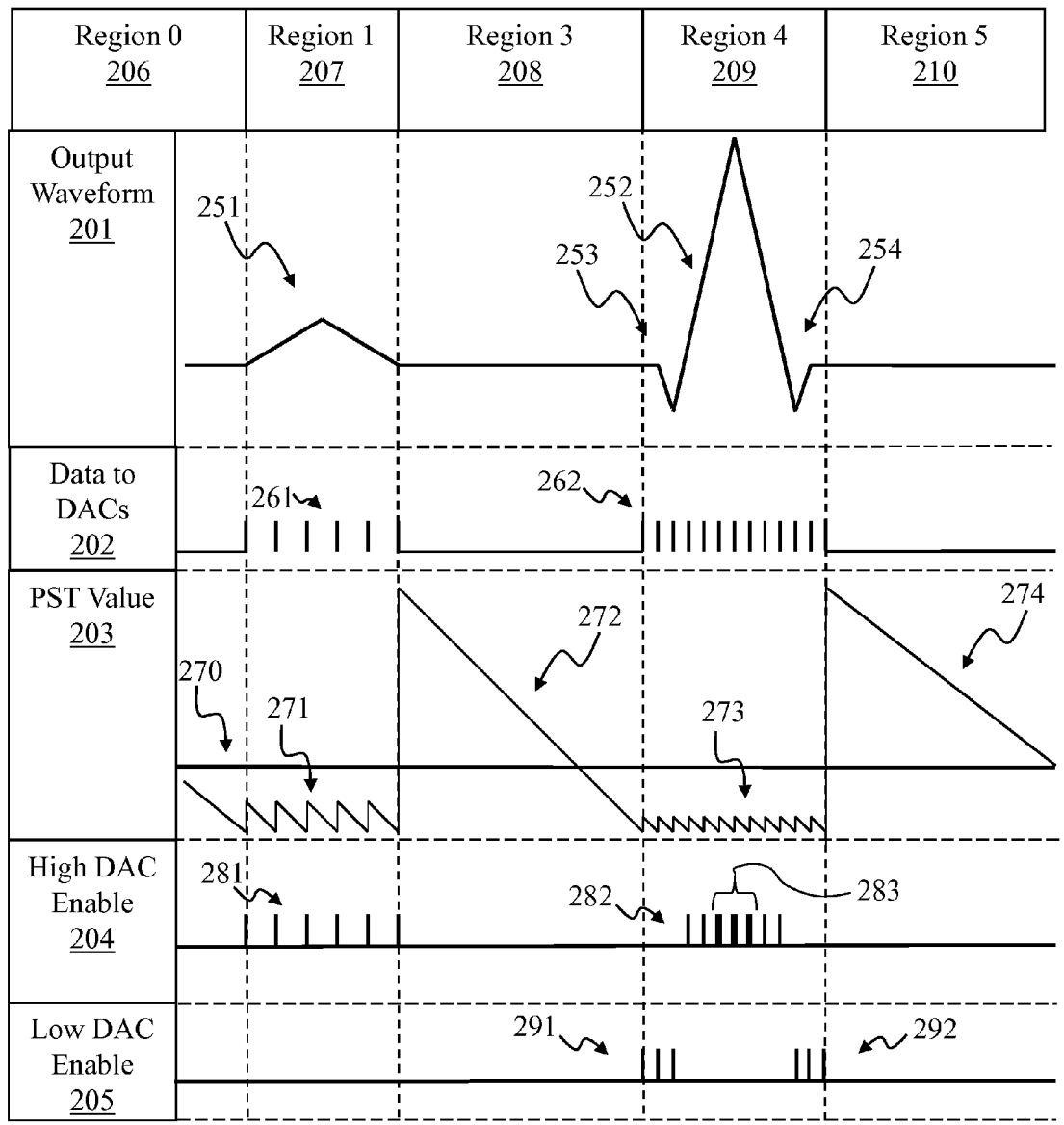
FIG. 2 is an exemplary strip chart of waveforms and signals across regions.

The simulator and the microcontroller in particular may have instruction loaded, or may have accessible memory, either or both of which may contain data or information reflective of a desired output waveform and particularly its profile which has particular features. The simulator generally attempts to output one or more of these waveforms and in doing so exploits one or more features of the profile of the waveform to economize on the power being used to generate such waveforms. Generation of an exemplary ECG signal is shown in FIG. 2. The output waveform 201, or desired output waveform profile, shown here may be described as having two features: following a first time range 206, or "Region 0," there is a low slope and amplitude feature 251 in a second time range 207, or "Region 1," and, following a third time range 208, or "Region 3," there is a high slope and amplitude feature 252 in a fourth time range 209, or "Region 4." The value of the programmable sleep timer (PST) 203 represents the time remaining until the microcontroller, particularly its oscillator, will be awakened from a sleeping state in that its normal oscillator is turned back on so that the microcontroller may again execute instructions responsive to the normal oscillator. In this example, the instruction execution, via the microcontroller, typically only occurs when the PST value is zero. During the entire time between the waveform features 206, 208, and 210 the PST value is non-zero 270, 272, 274 and both the microcontroller and the ECG DACs may be placed in very low power consumption sleep states.

During the time range of the low slope feature 251 in Region 1 207, the micro-controller is awakened from its very low power state with a moderate frequency, and values written 261 to the DACs 202. Once the DAC values are written, the PST value is written with a non-zero value 271. Because the waveform is positive, only the high DAC enable signal 204 need be used and the low DAC 205 can be remain shut down. The length of time that the DAC needs to be enabled may be quite short as the data will be held by the hold circuit 121 until the next DAC write may be made.

During the time range of the high slope feature 252 of Region 4 209, the microcontroller 102 is awakened from its low power state, and values 262 are written to the DACs 202 with a higher frequency so that the voltage granularity of the high slope feature is the same as the low slope feature. Once the DAC values are written, the PST value 203 is written with a non-zero value 273. At the edges 253, 254 of Region 4 209, the waveform feature goes negative so the High DAC enable 204 is left off and the Low DAC enable 205 is briefly pulsed on 291, 292 after each write of data to the DACs. During the center part of the high slope region, the waveform feature 252 is positive so the High DAC enable 204 may be used 282. As the waveform feature 252 grows in amplitude, the length, or the width when one references the timeline, of the High DAC enable pulses 283 increases to insure that the hold circuit 121 is fully charged to the brief peak of the waveform feature 252. The PST value (203) in this example is a function of the waveform feature where for the low slope feature 251, the PST durations 271 are of a moderate length, for a high slope feature 252, the PST durations 273 are of a smaller length, and for periods of no output waveform, the PST durations 270, 272, 274 are of a longer length.

Figure 3:
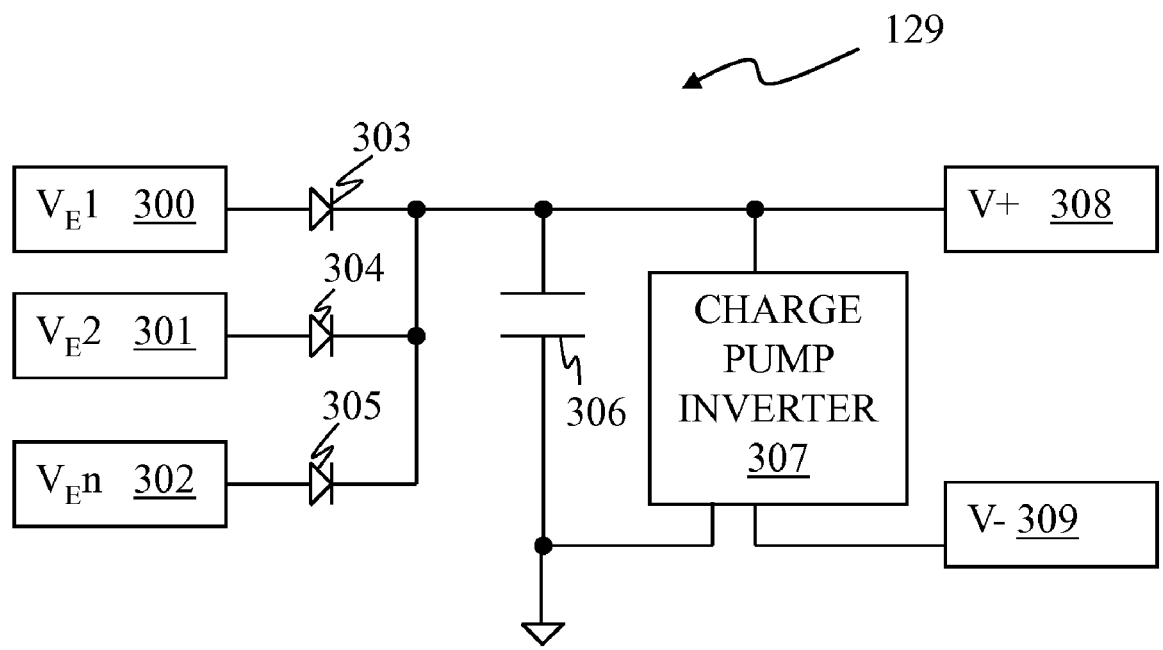
FIG. 3 is an exemplary circuit of an embodiment of the present invention.

Detail of the IBP power generation circuit 129 is shown in FIG. 3. The IBP power generation circuit 129 provides for the generation of positive supply voltage to power the IBP simulator and does so by drawing from an excitation signal path from, for example, a device under test, like a monitor, and provides for the generation of a negative supply voltage to provide a voltage reference signal for a multiplying DAC and does so from the same or a different excitation signal path from the monitor. This may be embodied by example with the switching of charged capacitors and is preferably embodied by the use of a charge pump inverter. Accordingly, the return path to the monitor is an excitation signal path. When in use, one or more invasive blood pressure transducer cables are connected to the device. Each connected transducer cable supplies an excitation voltage 300-302. These excitation voltages 300-302 may be of various DC voltages, or may be AC signals with various sine waves or, for example, square wave properties, voltages, and frequencies. The various excitation voltages are converted to positive DC signals via peak capture diodes 303-305 and a capacitor 306. The positive DC signal 308 is converted to a negative DC signal 309 via a charge pump inverter 307. The positive DC signal 308 supplies power to the ECG circuitry, for example, via power switch 134 (FIG. 1) and blood pressure simulating circuitry, and the negative DC signal 309 supplies negative power to the blood pressure simulating circuitry, e.g., the IBP1 DAC circuit 127 (FIG. 1).

Figure 4A:
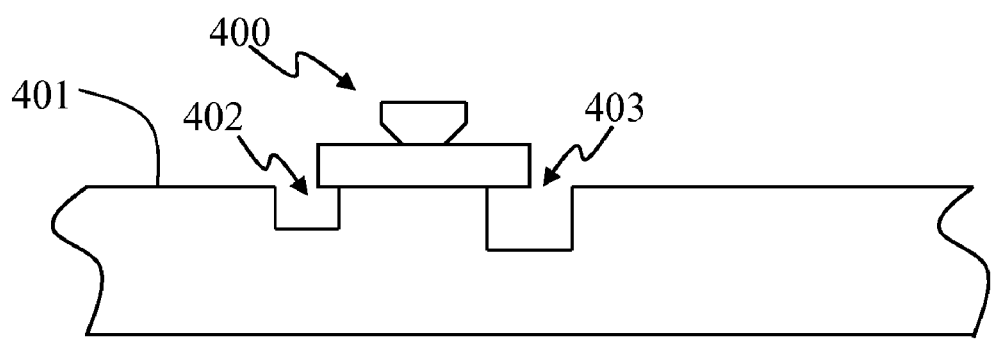
FIG. 4A is a side view of an exemplary mechanical receiving system embodiment of the present invention.
Figure 4B:
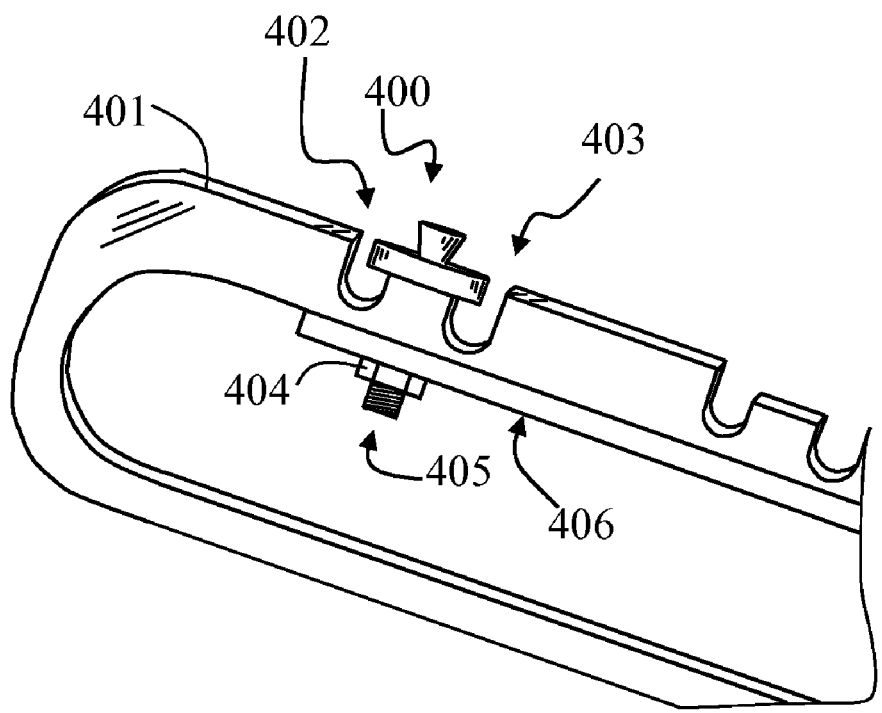
FIG. 4B is a side view of the exemplary mechanical receiving system embodiment of the present invention.
Figure 4C:
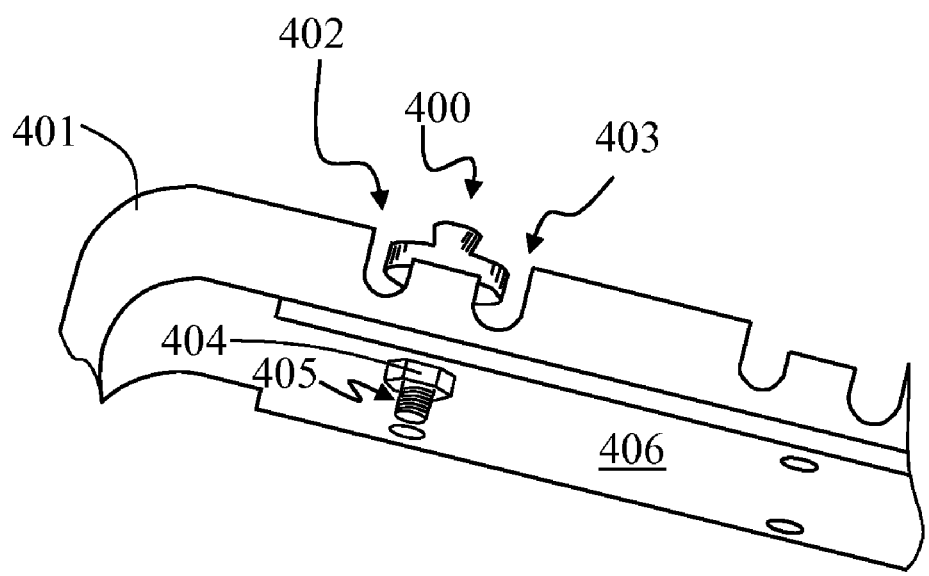
FIG. 4C is a bottom-side perspective view of the exemplary mechanical receiving system embodiment of the present invention.
Figure 4D:
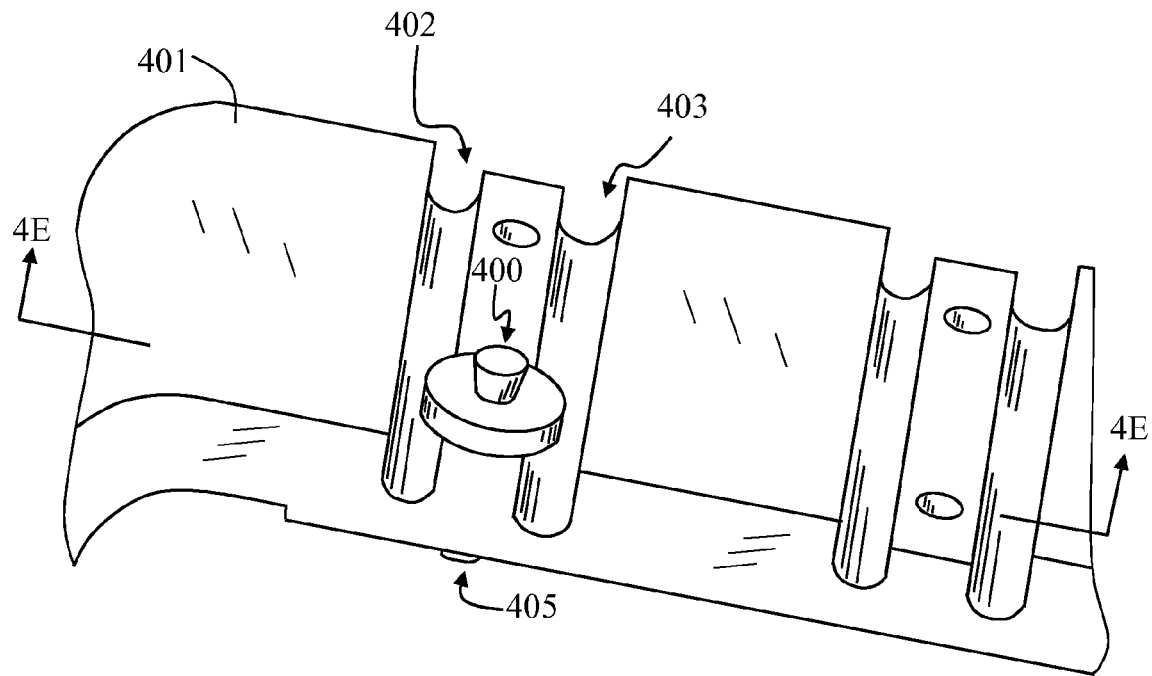
FIG. 4D is a top-side perspective view of the exemplary mechanical receiving system embodiment of the present invention.
Figure 4E:
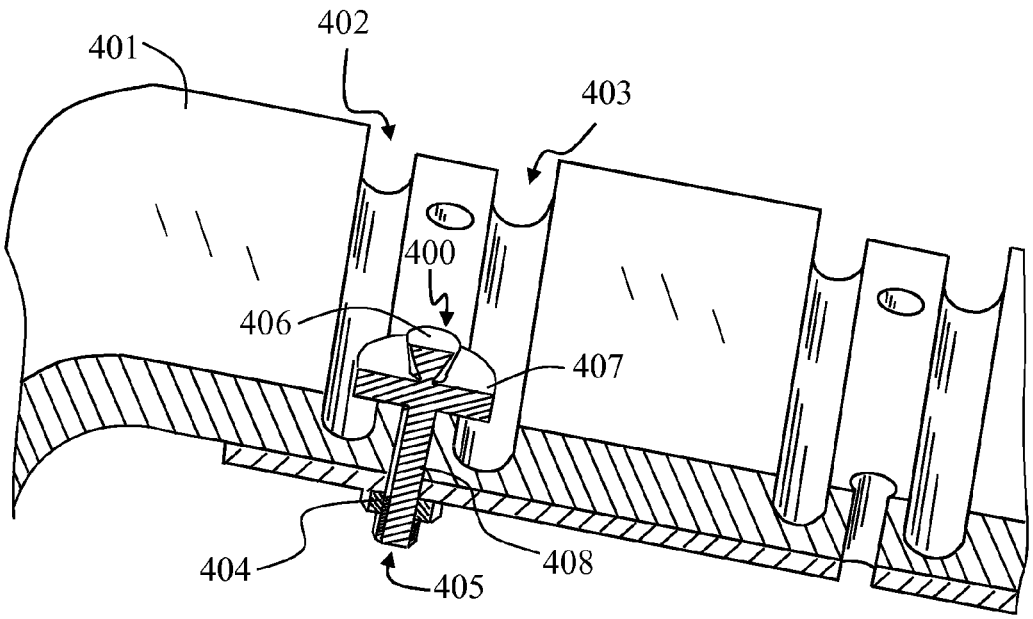
FIG. 4E is a top-side perspective view showing the exemplary mechanical receiving system embodiment of the present invention in cross-section.

Detail of the ECG connector is shown in FIG. 4A. The user may need to connect ECG devices to the simulator which may utilize various connector types, generally standard female snap type connectors or "banana jack" type connectors of two possible diameters. FIG. 4A shows the male ECG snap 400 on the simulator, which may be fastened to the simulator body 401 and thereby allows for the connection to a female snap connector. The simulator body 401 may also have two cavities 402 and 403, one on either side, and both adjacent to, the ECG snap 400, which allow a volume for the insertion of the various diameter banana jack connectors in such a way that they may be mechanically forced into electrical connection with the male ECG snap 400. FIG. 4B shows a side view where the means of fastening is shown in this example to be a threaded bolt portion 405 engaged by a nut 404 turned to secure itself against the under wall 406 of the simulator case 401. FIG. 4C shows a side-bottom perspective view of the male ECG snap 400 engaging the simulator body 401. FIG. 4D shows a side-top perspective view of the male ECG snap 400 engaging the simulator body 401. FIG. 4E is a cross-sectional view taken from FIG. 4D at reference 4E where portions of the male ECG snap 400 may be addressed. The exemplary male ECG snap 400 may be described as having an inverted frustroconical top portion 406, a disc portion 407, a cylindrical or barrel portion 408 that may or may not be threaded, and a threaded cylindrical portion 405. The exemplary male ECG snap 400 may be axisymmetric and thread through a cylindrical aperture that may be equidistant between the two cavities 402, 403 and the diameter of the disc portion 407 is typically longer than the width between the two cavities 402, 403 or grooves, thereby allowing for the engagement of various connectors.

Figure 5:
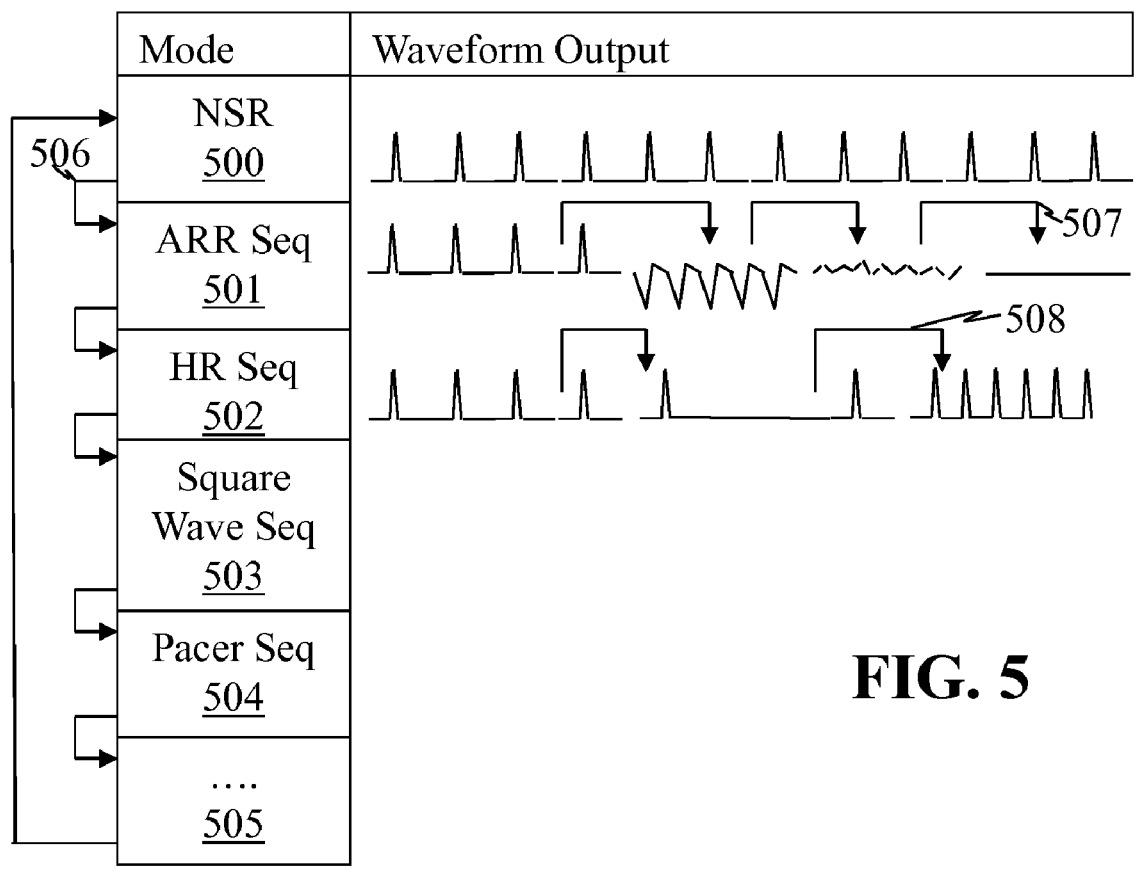
FIG. 5 is an exemplary strip chart of waveform outputs and modes for an embodiment of the present invention.

Detail of the user interface scheme is shown in FIG. 5. The simulator may be operated in several exemplary modes 500-505, each of which provides output of a specific simulated waveform. A single button press as shown as a directed arc 506 advances the unit to the next mode. In some of the modes such as the exemplary "ARR Sequence" 501 and the exemplary "HR Sequence" 502, the waveform may include a sequence of waveform types such that the simulator may output a specific waveform for a fixed number of simulated heart beats or a fixed time before transitioning on to a next specific waveform. The sequence of specific waveforms may represent either a physiologically significant sequence of events or a group of useful tests. While the simulator is performing one of these sequences the user may press and hold the user interface button for an extended period, typically a second or more, to activate what may be termed a "fast forward" function, as shown by the directed arcs 507 and 508. When activated, the fast forward function may operate to advance the simulation to the next specific waveform type of the sequence offered by the current mode. In some embodiments, the simulator may continue to output the next specific waveform type and not advance beyond that until the user again presses the button.

In another exemplary embodiment, the mode changing operation shown as arc 506 may be initiated by a double click of the button by the operator. For ease of use and to exploit user familiarity, the double click may have a timing interval similar to that of the double click of a computer mouse. As an aide to the operator, the mode LED may remain lit briefly on the release of the first click, and a second click while the LED is still lit is interpreted as a double click by the micro-processor, and, accordingly, a second click after the LED is turned off is interpreted as a successive single click.

The exemplary waveform advancements, shown as a first directed arc 507 and a second directed arc 508, may be initiated by a single click of the button. In such exemplary embodiments, the simulator may repeat a single waveform in the waveform sequence indefinitely, that is, until the mode button is single-clicked so as to advance the simulator to the next waveform.

The operation of "Push and Hold" of the mode button may effect a function that drives the invasive blood pressure waveforms to a 'zero' reference value for a period of time and may start other sequences.

Although this invention has been disclosed in the context of certain embodiments and examples, it will be understood by those or ordinary skill in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of ordinary skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

What is claimed is:

1. An electrical connector receiving system for a physiological waveform simulator comprising:
 a snap portion comprising:
  a disc portion having a top side, a bottom side and an edge; and
  the snap portion further comprising an inverted frustroconical portion fixedly attached to the top side of the disc portion; and
 a mounting element having a planar surface proximate to a first aperture; and
 wherein the bottom side of the disc portion is proximate to the planar surface of the mounting element, and a first sector of the bottom side of the disc portion extends over a portion of the first aperture so that a contact inserted into the first aperture may become electrically connected to the disc portion.

2. The electrical connector receiving system for a physiological waveform simulator of claim 1 wherein the planar surface of the mounting element is interposed between the first aperture and a second aperture; and wherein a second sector of the bottom side of the disc portion extends over a portion of the second aperture.

* * * * *